(12) United States Patent
Yamamoto et al.

(10) Patent No.: US 6,348,626 B1
(45) Date of Patent: Feb. 19, 2002

(54) PROCESS FOR PRODUCING OXAMIDE

(75) Inventors: Tomohiko Yamamoto; Yukio Inaba; Genji Koga; Hideki Noguchi; Joji Funatsu, all of Ube (JP)

(73) Assignee: Ube Industries, Ltd., Ube (JP)

( * ) Notice: Subject to any disclaimer, the term of this patent is extended or adjusted under 35 U.S.C. 154(b) by 0 days.

(21) Appl. No.: 08/112,478

(22) Filed: Aug. 27, 1993

Related U.S. Application Data

(63) Continuation of application No. 07/849,352, filed on Mar. 11, 1992, now abandoned.

(30) Foreign Application Priority Data

Mar. 15, 1991 (JP) .............................................. 3-128834

(51) Int. Cl.$^7$ ............................................. C07C 231/02
(52) U.S. Cl. ........................ 564/136; 564/134; 564/135

(56) References Cited

FOREIGN PATENT DOCUMENTS

| FI | WO 91/10643 | 7/1991 |
|----|-------------|--------|
| JP | 52-7916 | 1/1977 |
| JP | 52007916 | 5/1977 |

OTHER PUBLICATIONS

European Search Report dated Nov. 16, 1993.
Swedish Search Report dated Apr. 18, 1991.
Abstract 38941S, & JP–A–7707916 (UBE Industries, Ltd.) Jan. 21, 1997.

Chemical Abstracts, vol. 94, No. 21, May 25, 1981, (Columbus, Ohio U.S.) Okabe Taijiro et al: "Manufacturing process of oxamide", 651, abstract 174173q and Kaguku (Kyoto) 1980, 35(8)660–662.

Apr. 29, 1997 Official Action, Finnish Patent Application No. 921103 and English language translation.

Primary Examiner—Shailendra Kumar
(74) Attorney, Agent, or Firm—Finnegan, Henderson, Farabow, Garrett & Dunner, L.L.P.

(57) ABSTRACT

Oxamide is produced in a high purity by a process comprising (A) melting a starting material comprising 70 to 100 wt % of an oxalic acid diester of an aliphatic alcohol and 0 to 30 wt % of the same aliphatic alcohol as mentioned above, (B) feed-mixing an ammonia-containing gas to the starting material melt, while stirring, to produce oxamide and the aliphatic alcohol (by-product), (C) continuing the ammonia-feed-mixing procedure while controlling a feed rate of ammonia to an extent such that a content of the aliphatic alcohol in the reaction mixture is maintained at a level of 3 to 45% by weight, to produce a wetted solid reaction product comprising the resultant oxamide and the aliphatic alcohol, and then (D) collecting the oxamide from the reaction product by evaporating away the aliphatic alcohol.

11 Claims, No Drawings

PROCESS FOR PRODUCING OXAMIDE

This application is a continuation of application Ser. No. 07/849,352 filed Mar. 11, 1992, now abandoned.

BACKGROUND OF THE INVENTION

1) Field of the Invention

The present invention relates to a process for producing oxamide (oxalic acid diamide) of the formula $(CONH_2)_2$. More particularly, the present invention relates to a process for producing oxamide in a solid state with a high degree of purity by a one step reaction of an oxalic acid diester with ammonia under specific industrial conditions.

2) Description of the Related Arts

As a typical process for producing oxamide Japanese Unexamined Patent Publication No. 52-7,916 discloses a process comprising the steps of mixing an aliphatic alcohol with oxalic acid diester under specific conditions, then adding ammonia to the mixture to cause the oxalic acid diester to react with ammonia and produce oxamide.

In the above-mentioned process, the production of oxamide from an oxalic acid diester with ammonia is carried out in accordance with the following chemical reaction:

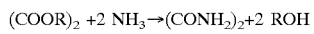
$(COOR)_2 + 2\ NH_3 \rightarrow (CONH_2)_2 + 2\ ROH$ wherein R represents a lower alkyl group having 1 to 6 carbon atoms, for example, a methyl, ethyl, propyl, butyl or pentyl group.

In the above-mentioned conventional process, the reaction of an oxalic acid diester with ammonia is carried out in a solution system containing an excessive amount of an aliphatic alcohol. This excessive amount of aliphatic alcohol exhibits an effect of restricting the production of a by-product consisting of oxalic acid monoestermonoamide during the above-mentioned reaction procedure, and therefore, the conventional process can produce oxamide with a high degree of purity at a high yield.

As mentioned above, the production of oxamide is carried out in a liquid phase reaction system which always contains an excessive amount of an aliphatic alcohol.

Also, the resultant oxamide is significantly insoluble in the aliphatic alcohol. Therefore, when the oxamide-producing reaction is completed, the resultant reaction mixture is in the state of a slurry of the oxamide particles. To obtain a high purity oxamide, it is necessary to collect the oxamide particles from the slurry, by filtration, and remove the aliphatic alcohol mixed with the collected oxamide particles by a drying procedure at a high temperature. Namely, the conventional process for producing oxamide is disadvantageous in that the resultant oxamide must be purified by complicated refining procedures and apparatuses, and a large amount of heat energy must be consumed by these refining procedures.

SUMMARY OF THE INVENTION

An object of the present invention is to provide a process for producing oxamide by a reaction of an oxalic acid diester with ammonia, by a simple procedure and apparatus with a saving of heat energy consumption.

Another object of the present invention is to provide a process for producing oxamide having a high degree of purity at a high yield.

The above-mentioned objects can be attained by the process of the present invention for producing oxamide, comprising the steps of:

(A) melting a starting material comprising 70 to 100% by weight of an oxalic acid diester of an aliphatic alcohol and 0 to 30% by weight of the same aliphatic alcohol as mentioned above;

(B) feed-mixing an ammonia-containing gas to the resultant melt of the starting material, while stirring, to start a reaction of the oxalic acid diester of the aliphatic alcohol with ammonia to produce oxamide and a by-product consisting of the aliphatic alcohol;

(C) continuing the feed-mixing procedure of the ammonia-containing gas, while stirring and controlling a feed rate of ammonia to an extent such that a content of the aliphatic alcohol in the resultant reaction mixture is maintained at a level of 3 to 45% by weight, to provide a reaction product in the state of a wetted solid and containing the resultant oxamide and the aliphatic alcohol; and (D) collecting the oxamide from the reaction product by evaporating away the aliphatic alcohol.

DESCRIPTION OF THE PREFERRED EMBODIMENTS

In the first step of the process of the present invention, a starting material is prepared by mixing 70 to 100%, preferably 80 to 100%, more preferably 85 to 98% by weight of an oxalic acid diester of an aliphatic alcohol with 0 to 30%, preferably 0 to 20%, more preferably 2 to 15% by weight of the same aliphatic alcohol as mentioned above, and uniformly melting the resultant mixture at a melting temperature of the mixture or more. For example, a starting material consisting of a mixture of dimethyl oxalate and methyl alcohol is melted at a temperature of 40° C. to 60° C.

The aliphatic alcohol preferably has 1 to 6 carbon atoms and is selected from methyl alcohol, ethyl alcohol, n- and iso-propyl alcohols, n-, iso-, and sec-butyl-alcohol, pentyl alcohols and hexyl alcohols.

The melt of the starting material is subjected to the second step of the process of the present invention.

In the second step, an ammonia-containing gas is fed to and mixed with the melt of the starting material, while stirring the reaction mixture, to start a reaction of the oxalic acid diester of the aliphatic alcohol with ammonia to produce oxamide and a by-product consisting of the aliphatic alcohol, preferably at a temperature of 40° C. to 160° C.

In the third step, the feed mixing procedure of the ammonia-containing gas to the reaction mixture is continued while stirring the reaction mixture and controlling the feed rate of ammonia to an extent such that a content of the aliphatic alcohol in the reaction mixture is maintained at a level of 3 to 45% by weight, preferably 5 to 40% by weight, more preferably 10 to 30% by weight, to provide a reaction product in the state of a wetted solid and containing oxamide in a high degree of purity and the aliphatic alcohol. Preferably, the reaction product is in the state of a solid powder.

The ammonia-containing gases include a 100% ammonia gas and mixed gas of ammonia with an inert gas, for example, nitrogen gas, carbon dioxide gas or argon gas. Preferably, the ammonia-containing gas contains ammonia in a content of at least 50% by volume, more preferably at least 60% by volume.

During the third step, the state of the reaction mixture is successively changed from a melt (liquid) to a paste and then a solid, preferably a solid powder, with a progress of the reaction.

At the initial stage of the reaction, the reaction mixture contains non-reacted oxalic acid diester in a large content.

With the progress of the reaction of the oxalic acid diester with ammonia, the content of the oxalic acid diester in the reaction mixture is decreased and the content of the reaction products of the oxalic acid diester with ammonia, for example, oxalic acid monoestermonoamide and oxamide is increased. In the final stage of the third step, the content of the oxalic acid monoestermonoamide is decreased, due to the further reaction thereof with ammonia, and becomes substantially zero. Therefore, the final reaction product contains oxamide with a high purity.

In the reaction of the oxalic acid diester with ammonia, the reaction mixture in the state of a melt (liquid), paste or solid is forcibly agitated. This forcible agitation is not restricted to a specific operation as long as the reaction mixture is placed under conditions in which ammonia can be effectively absorbed by the reaction mixture, and can be effected by a conventional agitating operation, for example, stirring, dispersing, kneading, knead-mixing or admixing.

For example, the forcible agitation is carried out by using a ball mill type reactor in which a number of balls, for example, glass balls, ceramic balls, or metal balls, are placed and the reaction mixture is agitated by vigorous movements of the balls, or a rotary kiln type reactor in which the reaction mixture is agitated by paddles or chains fixed in the reactor, or another type of reactor with agitating blades having a shape and size effective for satisfactorily mixing ammonia with the reaction mixture.

Also, the forcible agitating means preferably has, in addition to the agitating and mixing functions, a grinding function and a drying function for the resultant solid product. This type of forcible agitating means is useful for finally obtaining oxamide powder having a uniform quality by a simple operation.

Further, it is important that the feed-mixing operation of an ammonia gas be continued while the content of the aliphatic alcohol in the reaction mixture is contained at a level of from 3 to 45% by weight. This step is effective for obtaining oxamide with a high purity while restricting the production of a by-product consisting of oxalic acid monoestermonoamide.

When the content of the aliphatic alcohol in the reaction mixture becomes more than 45% by weight, the final reaction product is in the state of a slurry, and therefore, the resultant oxamide must be collected by complicated separating steps, for example, a filtering for separating oxamide from the slurry, and a drying step for drying the filtered oxamide.

When the content of the aliphatic alcohol in the reaction mixture becomes less than 3% by weight, the resultant final product contains a relatively large amount of oxalic acid monoestermonoamide, which affects a growth of a plant when oxamide is employed as a slow release fertilizer for the plant.

In consideration of the reaction temperature, reaction pressure, and the feeding rate of ammonia, the content of the aliphatic alcohol in the reaction mixture is adjusted to a desired level by controlling the amount of the aliphatic alcohol produced as a by-product of the ammonia-addition-decomposition reaction of the oxalic acid diester, and the amount of the aliphatic alcohol evaporated from the reaction product.

Where the initial content of the aliphatic alcohol in the starting material melt is relatively high, the starting material can be melted at a relatively low temperature, and thus the production of the undesirable by-product consisting of oxalic acid monoestermonoamide in the initial stage of the reaction can be restricted, and the reaction efficiency of ammonia with the oxalic acid diester can be increased.

Nevertheless, the content of the aliphatic alcohol in the reaction mixture may become more than 45% by weight, due to the production of a by-product consisting of the aliphatic alcohol and produced by the reaction of the oxalic acid diester with ammonia. To avoid an excess of the content of the aliphatic alcohol over 45% by weight, the reaction procedure is preferably carried out while positively evaporating away the by-product consisting of the aliphatic alcohol by utilizing a heat of the reaction. Namely, the content of the aliphatic alcohol in the reaction mixture must be controlled to a level of from 3% to 45% by weight throughout the reaction procedure.

In the process of the present reaction, the reaction mixture must be maintained at a reaction temperature at which the mixture of the non-reacted oxalic acid diester and the aliphatic alcohol can be maintained in the state of a melt, and the content of the aliphatic alcohol therein can be maintained within the above-mentioned range (3 to 45% by weight). For example, where the starting material consists of dimethyl oxalate and methyl alcohol, the reaction temperature is preferably controlled to a level of from 40° C. to 160° C., more preferably 45° C. to 65° C.

The reaction of the oxalic acid diester with ammonia is preferably carried out under the ambient atmospheric pressure, but the reaction can be carried out under a reduced pressure or a pressure higher than the ambient atmospheric pressure.

When the by-product consisting of an aliphatic alcohol is evaporated and separated from the reaction mixture, the separated aliphatic alcohol is cooled in a cooler and recovered as a condensed liquid.

The recovered aliphatic alcohol can be reused in the process for producing oxamide.

The reaction procedure is continued for a time long enough to produce oxamide with a high purity by an ammonia-addition and decomposition reaction of the oxalic acid diester under the above-mentioned reaction conditions. Usually, the reaction time is 0.5 to 5 hours, preferably 1 to 3 hours.

It is clear that the oxamide-producing process of the present invention can be carried out in a batch type procedure, but the process of the present invention also can be carried out continuously by combining a continuous procedure for preparing an oxalic acid diester-containing starting material melt with a continuous feeding procedure of an ammonia-containing gas, a continuous stirring procedure for the reaction mixture, and a continuous procedure for collecting the resultant solid oxamide with a high purity.

The solid reaction product of the process of the present invention contains oxamide with a high degree of purity of 98% by weight or more, preferably 99% by weight or more. Also, in the solid reaction product of the process of present invention, an existence of undesirable oxalic acid monoestermonoamide is not detected. Therefore, when used as a slow release fertilizer for a plant, the reaction product of the process of the present invention substantially does not affect the growth of the plant.

In the process of the present invention, the reaction procedure can be continued while grinding the reaction mixture to produce a solid oxamide product. Therefore, the resultant oxamide product is in the form of an even powder and has a uniform quality.

The oxamide powder can be formed into granules having a desired size, by using a binder. The oxamide granules are useful for a slow release fertilizer for plants. The process of the present invention enables oxamide to be produced in a high yield and from oxalic acid diester and ammonia, by energy-saving procedures by which oxamide solid particles having a high degree of purity can be collected without consuming a specific heat energy.

Namely, in the process of the present invention, the conventional step for collecting and purifying the resultant oxamide powder from the reaction mixture is not necessary, and the resultant oxamide powder has a high degree of purity.

EXAMPLES

The present invention will be further explained by the following specific examples.

Example 1

A rotary evaporator having a capacity of 500 ml, equipped with an oil bath at a temperature of 45° C. and containing therein glass balls with a diameter of 1 cm, was charged with 50 g of dimethyl oxalate and 5.6 g of methyl alcohol to provide a starting material having a melting point of 43° C.

The starting material was melted at a temperature of 45° C.

While the rotary evaporator was rotated at speed of 100 rpm, an ammonia gas was fed in an average feed rate of 0.45 liter/min calculated under a standard temperature (0° C.) and pressure (1 atm.), to start the ammonia-addition and decomposition reaction of the dimethyl oxalate.

The feed of the ammonia gas was continued for 180 minutes.

The resultant solid reaction product was removed from the evaporator and dried in a vacuum dryer under a reduced pressure of 3 mmHg at a temperature of 40° C. for 12 hours, to evaporate and remove methyl alcohol from the solid reaction product.

The resultant powdery product was 37.0 g of high purity oxamide.

In the above-mentioned reaction procedure, the content of methyl alcohol in the reaction mixture was 24.9% by weight at 60 minutes after the start of the reaction, 21.7% of weight at 120 minutes after the start of the reaction and 18.8% by weight at 180 minutes after the start of the reaction.

Also, in the reaction, the powdery product was obtained in an yield of 98.6% based on the molar amount of the dimethyl oxalate.

The compositions of the reaction mixture and product are shown in Table 1. Also, Table 1 shows a nitrogen analysis result and oxamide purity of the resultant powdery product.

Example 2

The same procedures as in Example 1 were carried out, with the following exceptions.

The average feed rate of the ammonia gas was 0.34 liter/minute when determined under the standard temperature and pressure.

The temperature of the oil bath was 60° C.

After 60 minutes from the start of the reaction, the temperature of the oil bath was gradually elevated to 170° C., to evaporate and remove the generated by-product consisting of methyl alcohol from the reaction product.

A powdery solid product comprising oxamide with a high purity was obtained in an amount of 36.7 g, without the drying procedure.

The results of the same tests as in Example 1 are indicated in Table 1.

Example 3

The same procedures as in Example 1 were carried out, with the following exceptions.

The content of methyl alcohol in the starting material melt was zero.

The temperature of the oil bath was 65° C.

The average feed rate of the ammonia gas was 0.46 liter/minute, when determined under the standard temperature and pressure.

The feed time of the ammonia gas (reaction time) was 120 minutes.

The powdery solid product comprising high purity oxamide was obtained in an amount of 36.5 g.

The results of the same measurements as made in Example 1 are shown in Table 1.

Comparative Example 1

A flat-bottomed separable flask was charged with a mixture of 300 g of methyl alcohol with 35.4 g of dimethyl oxalate. Then, while the mixture was stirred at a constant temperature of 20° C., an ammonia gas was fed at an average feed rate of 300 ml/minute under the standard temperature and pressure into the mixture for 45 minutes. The reaction procedure was further continued at a temperature of 20° C. for 60 minutes.

When the reaction procedure was completed, it was found that the reaction mixture was in the state of a slurry in which oxamide particles were dispersed in methyl alcohol.

The slurry was subjected to filtration through a filter paper sheet, to collect the oxamide particles.

The filtered oxamide particles contained methyl alcohol in an amount of about 50% of weight. Thus, the filtered oxamide particles were heated at a temperature of 110° C., to evaporate and remove methyl alcohol wherefrom.

The resultant oxamide powder was in an amount of 25.9 g.

The results of the same measurements as in Example 1 are indicated in Table 1.

TABLE 1

| Item Example No. | Composition of starting material - Dimethyl oxalate (g) | Composition of starting material - Methyl alcohol (g) | Ammonia gas Feed rate (liter/min) | Reaction conditions - Temperature of oil bath (°C.) | Reaction conditions - Reaction pressure | Reaction time (min) | Composition of reaction mixture - Dimethyl oxalate (wt %) | Composition of reaction mixture - Oxalic acid monomethyl ester monoamide (wt %) | Composition of reaction mixture - Methyl alcohol (wt %) | Nitrogen analysis result (%) (*)¹ | Purity of oxamide (%) (*)² |
|---|---|---|---|---|---|---|---|---|---|---|---|
| Example 1 | 50 | 5.6 | 0.45 | 45 | Ambient atmospheric pressure | 60 | 0.0 | 66.5 | 24.9 | — | — |
|  |  |  |  |  |  | 120 | 0.0 | 0.0 | 31.7 | — | — |
|  |  |  |  |  |  | 180 | 0.0 | 0.0 | 18.8 | — | — |
|  |  |  |  |  | Dried |  | 0.0 | 0.0 | 0.0 | 31.6 | 99.4 |
| Example 2 | 50 | 5.6 | 0.34 | 60 60–170 | Ambient atmospheric pressure | 60 | 0.0 | 2.3 | 22.4 | — | — |
|  |  |  |  |  |  | 180 | 0.0 | 0.0 | 0.0 | 31.5 | 99.1 |
| Example 3 | 50 | 0 | 0.46 | 65 | Ambient atmospheric pressure | 60 | 0.0 | 10.2 | 24.0 | — | — |
|  |  |  |  |  |  | 90 | 0.0 | 0.0 | 21.5 | — | — |
|  |  |  |  |  |  | 120 | 0.0 | 0.0 | 14.5 | — | — |
|  |  |  |  |  | Dried |  | 0.0 | 0.0 | 0.0 | 31.3 | 98.4 |
| Comparative Example 1 | 35.4 | 300 | 0.3 | 20 | Ambient atmospheric pressure | 45 | — | — | — | — | — |
|  |  |  |  |  | Dried |  | 0.0 | 0.0 | 0.0 | 31.7 | 99.7 |

Note:
(*)¹ Nitrogen content measured by the Kjeldahl method. The theoretical nitrogen content of oxamide is 31.8% by weight.
(*)² The purity of oxamide was calculated from the measured nitrogen content of the product.

Table 1 clearly indicates that the products of the process of the present invention contained oxamide in a very high degree of purity, and substantially no oxalic acid monoestermonoamide.

Accordingly, the products of the process of the present invention are useful as a slow release fertilizer for plants, and are free from an undesirable effect of the oxalic acid monoestermonoamide, which affects the growth of the plant.

What is claimed is:

1. A process for producing oxamide comprising the step of:
   (a) melting a starting material consisting essentially of 70 to 100% by weight of an oxalic acid diester of an aliphatic alcohol and 0 to 30% by weight of the same aliphatic alcohol as mentioned above;
   (b) feed-mixing an ammonia-containing gas to the resulting melt of the starting material, while stirring, to start a reaction of the oxalic acid diester of the aliphatic alcohol with ammonia to produce oxamide and a by-product consisting of the aliphatic alcohol;
   (c) continuing the feed-mixing procedure of the ammonia-containing gas under reaction conditions sufficient to convert said diester to oxamide and, while stirring, controlling the feed rate of ammonia, and evaporating and removing the aliphatic alcohol by-product from the reaction mixture to an extent such that the content of the aliphatic alcohol in the reaction mixture is maintained at a level of 5 to 40% by weight to produce a reaction product mixture containing the resulting oxamide and the aliphatic alcohol substantially free of oxalic acid monoestermonoamide, and wherein said reaction product mixture is in the state of a wetted solid without filtering it; and
   (d) directly drying the reaction product mixture in the state of a wetted solid to remove the aliphatic alcohol from said wetted solid and recover said oxamide.

2. The process as claimed in claim 1, wherein the aliphatic alcohol has 1 to 6 carbon atoms.

3. The process as claimed in claim 1, wherein in the melting step (A), the starting material is melted at a temperature of from 40° C. to 160° C.

4. The process as claimed in claim 1, wherein the ammonia-containing gas contains ammonia in an amount of 50% by volume or more.

5. The process as claimed in claim 1, wherein the reaction of the oxalic acid diester with ammonia is carried out at a temperature of from 40° C. to 160° C.

6. The process as claimed in claim 1, wherein during the reaction of the oxalic acid diester with ammonia, the content of the aliphatic alcohol in the resultant reaction mixture is from 10 to 40% by weight.

7. The process as claimed in claim 1, wherein the reaction of the oxalic acid diester with ammonia is carried out at a temperature of from 40 to 160° C.

8. The process as claimed in claim 1, wherein the oxalic acid diester is dimethyl oxalate and the aliphatic alcohol is methyl alcohol.

9. The process as claimed in claim 8, wherein the reaction of the dimethyl oxalate with ammonia is carried out at a temperature at which the mixture of the non-reacted dimethyl oxalate and the methyl alcohol is maintained in a melted state.

10. The process as claimed in claim 1, wherein said starting material is a starting material consisting essentially of 85 to 100% by weight of the oxalic acid diester of the aliphatic alcohol and 0 to 15% by weight of the same aliphatic alcohol as mentioned above.

11. A process for producing oxamide comprising the step of:
   (a) melting a starting material consisting essentially of an oxalic acid diester of an aliphatic alcohol and the same aliphatic alcohol as mentioned above;

(b) feed-mixing an ammonia-containing gas to the resultant melt of the starting material, while stirring, to start a reaction of the oxalic acid diester of the aliphatic alcohol with ammonia to produce oxamide and a by-product consisting of the aliphatic alcohol;

(c) continuing the feed-mixing procedure of the ammonia-containing gas under reaction conditions sufficient to convert said diester to oxamide and, while stirring, controlling the feed rate of ammonia to an extent such that the content of the aliphatic alcohol in the resultant reaction mixture is maintained at a level of 5 to 40% by weight, to produce a reaction product mixture containing the resulting oxamide and aliphatic alcohol substantially free of oxalic acid monoestermonoamide, and wherein said reaction product mixture is in the state of a wetted solid without filtering it; and (d) directly drying the reaction product mixture in the state of a wetted solid to remove the aliphatic alcohol from said wetted solid and recover said oxamide.

* * * * *